United States Patent [19]

Kraft et al.

[11] Patent Number: 4,959,384
[45] Date of Patent: Sep. 25, 1990

[54] USE OF NITROFURANTOIN FOR THE TREATMENT AND PROPHYLAXIS OF GASTROINTESTINAL DISORDERS

[75] Inventors: William G. Kraft, Norwich; Donna R. Morgan, Sherburne, both of N.Y.

[73] Assignee: Norwich Eaton Pharmaceuticals, Inc., Norwich, N.Y.

[21] Appl. No.: 790,919

[22] Filed: Oct. 24, 1985

[51] Int. Cl.$^5$ .............................................. A61K 31/415
[52] U.S. Cl. ...................................... 514/390; 514/927
[58] Field of Search ............................................ 514/390

[56] References Cited

PUBLICATIONS

Physicians' Desk Reference (PDR), 38 Edition, pp. 3395–1936, (1984).
Marshall, B. J., "*Campylobacter pyloridis* and Gastritis", *The Journal of Infectious Diseases*, vol. 153, No. 4, (Apr. 1986), pp. 650–657.
Goodwin, C. S., J. A. Armstrong and B. J. Marshall, "*Campylobacter pyloridis*, Gastritis, and Peptic Ulceration", *Journal of Clinical Pathology*, vol. 39, No. 4, (Apr. 1986), pp. 353–365.
Smith, J. S., G. E. Buck and D. Niesel, "Genetic Relationship of *Campylobacter pyloridis* to Other Species of Campylobacter", *Abstracts of the Annual Meeting*, American Society of Microbiology, 1985, p. 94.
McNulty, C. A. M., B. Crump, J. C. Gearty, M. Davis, I. A. Donovan, M. D. Manhart and R. Wise, "Successful Therapy of *Campylobacter pyloridis* Gastritis", *Gastroenterology*, May 1986, p. 1547.
McNulty, C. A. M., J. Dent and R. Wise, "Susceptibility of Clinical Isolates of *Campylobacter pyloridis* to 11 Antimicrobial Agents", *Antimicrobial Agents and Chemotherapy*, vol. 28, No. 6, (Dec. 1985), pp. 837–838.
Carlson, J. R., S. A. Thornton, H. L. DuPont, A. H. West and J. J. Mathewson, "Comparative in Vitro Activities of Ten Antimicrobial Agents Against Bacterial Enteropathogens", *Antimicrobial Agents and Chemotherapy*, vol. 24, No. 4, (Oct. 1983), pp. 509–513.
Vanhoff, R., B. Gordts, R. Dierickx, H. Coignau and J. P. Butzler, "Bacteriostatic and Bactericidal Activities of 24 Antimicrobial Agents Against *Campylobacter fetus* Subsp. *Jejuni*", *Antimicrobial Agents and Chemotherapy*, vol. 18, No. 7, (Jul. 1980), pp. 118–121.
Karmali, M. A., S. De Grandis and P. C. Fleming, "Antimicrobial Susceptibility of *Campylobacter jejuni* and Special Reference to Resistance Patterns of Canadian Isolates", *Antimicrobial Agents and Chemotherapy*, vol. 19, No. 4, (Apr. 1981), pp. 593–597.
Blaser, M. J., and L. B. Reller, "Campylobacter Enteritis", *The New England Journal of Medicine*, vol. 305, No. 24, (Dec. 10, 1981), pp. 1444–1452.
Warren, J. R., "Unidentified Curved Bacilli on Gastric Epithelium in Active Chronic Gastritis", *The Lancet*, vol. 1, (Jun. 4, 1983), p. 1273.
Marshall, B., "Unidentified Curved Bacilli on Gastric Epithelium in Active Chronic Gastritis", *The Lancet*, vol. 1, (Jun. 4, 1983), pp. 1273–1275.
McNulty, C. A. M., and D. M. Watson, "Spiral Bacteria of the Gastric Antrum", *The Lancet*, vol. 1, (May 12, 1984), pp. 1068–1069.
Marshall, B. J., and J. R. Warren, "Unidentified Curved Bacilli in the Stomach of Patients with Gastritis and Peptic Ulceration", *The Lancet*, vol. 1, (Jun. 16, 1984), pp. 1311–1315.
Langenberg, M. L., G. N. J. Tytgat, M. E. I. Schipper, P. J. G. M. Rietra and H. C. Zanen, "Campylobacter–Like Organisms in the Stomach of Patients and Healthy Individuals", *The Lancet*, vol. 1, (Jun. 16, 1984), p. 1348.
Burnett, R. A., J. A. H. Forrest, R. W. A. Girdwood and C. R. Fricker, "Campylobacter–Like Organisms in the Stomach of Patients and Healthy Individuals", *The Lancet*, vol. 1, (Jun. 16, 1984), p. 1349.
Marshall, B. J., D. B. McGechie, G. J. Francis and P. G. Utley, "Pyloric Campylobacter Serology", *The Lancet*, vol. 2, (Aug. 4, 1984), p. 281.
McLean, A. J., P. M. Harrison, L. L. Ioannides-Demos, A. J. Byrne, P. McCarthy and F. J. Dudley, "Microbes, Peptic Ulcer and Relapse Rates with Different Drugs", *The Lancet*, vol. 2, (Sep. 1, 1984), pp. 525–526.
Marshall, B. J., D. B. McGechie, P. A. Rogers and R. J. Glancy, "Pyloric Campylobacter Infection and Gastroduodenal Disease", *The Medical Journal of Australia*, vol. 142, (Apr. 15, 1985), pp. 439–444.
Zheng, Z. T., Z. Y. Wang, Y. X. Chu, Y. N. Li, Q. F. Li, S. R. Lin and Z. M. Xu, "Double-Blind Short-Term Trial of Furazolidone in Peptic Ulcer", *The Lancet*, vol. 1, (May 4, 1985), pp. 1048–1049.
McNulty, C. A. M., and R. Wise, "Rapid Diagnosis of Campylobacter-Associated Gastritis", *The Lancet*, vol. 1, (Jun. 22, 1985), pp. 1443–1444.
Flores, B. M., C. L. Fennell, K. K. Holmes and W. E. Stamm, "In Vitro Susceptibilites of Campylobacter–Like Organisms to Twenty Antimicrobial Agents", *Antimicrobial Agents and Chemotherapy*, vol. 28, No. 2, (Aug. 1985), pp. 188–191.
Jones, D. M., A. Curry and A. J. Fox, "An Ultrastructural Study of the Gastric Campylobacter–Like Organism '*Campylobacter pyloridis*'", *Journal of General Microbiology*, vol. 131, (1985), pp. 2335–2341.
Shirokova, K. I., R. M. Filimonov and L. V. Poliakova, "The Use of Metronidazole in Treatment of Patients (List continued on next page.)

*Primary Examiner*—Frederick E. Waddell
*Attorney, Agent, or Firm*—Milton B. Graff, IV; Jack D. Schaeffer; Richard C. Witte

[57] ABSTRACT

The invention involves methods for the treatment and prophylaxis of human or animal subjects having infectious gastrointestinal disorders of the upper gastrointestinal tract caused or mediated by Campylobacter-like organisms comprising the step of administering to the subjects safe and effective amounts of nitrofurantoin.

11 Claims, No Drawings

OTHER PUBLICATIONS with Ulcerative Disease", *Klin. Med.,* (Mosk), vol. 59, No. 2, (Feb. 1981), pp. 48–50.

Zheng, Z. T., Z. Y. Wang, Y. X. Chu, Z. M. Xu, Z. X. Li, X. W. Dong and Z. J. Wang, "Treatment of Gastrointestinal Ulcer by Furazolidone", *Chinese Journal of Digestion,* vol. 2, (1982), pp. 131–133.

Lu, L., F. Zhou and J. Yu, "Effect of Furaxon and its Analogs on Gastrointestinal Propulsion in Mice", *Beijing Yixueyuan Xuebao,* vol. 15, No. 3, (1983), pp. 185–187.

Zheng, Z. T., T. Y. Wang, Y. S. Zhu, Y. Y. Lee, J. F. Lee, S. Z. Lin and G. M. Xu, "A Double-Blind Short-Term Clinical Trial of the Effect of Furazolidone on Peptic Ulcer", *Chinese Journal of Internal Medicine,* vol. 23, No. 4, (Apr. 1984), pp. 195–197.

He, B. E. and S. C. He, "Cytoprotection of Furazolidone in Restraint-Soakage Gastric Ulcers in Rats", *Jinan Liyi Xuebao,* vol. 4, (1984), pp. 55–59.

Zhang, S., J. Shao and Y. Yu, "Protective Effects of Furazolidone and Some Commonly Used Antiulcer Drugs on Several Gastric Ulcer Models in Rats", *Yaoxue Xuebao,* vol. 19, No. 1, (1984), pp. 5–11.

USE OF NITROFURANTOIN FOR THE TREATMENT AND PROPHYLAXIS OF GASTROINTESTINAL DISORDERS

TECHNICAL FIELD

The present invention relates to methods for the treatment and prophylaxis of infectious gastrointestinal disorders in humans and other animals.

BACKGROUND OF THE INVENTION

Factors adversely affecting the function of the gastrointestinal system in humans are exceedingly varied in their nature. Such disorders may arise in the upper or lower gastrointestinal tracts or both. There is a broad range of causes of gastrointestinal disorders, including genetic, physiological, environmental, and psychogenic factors. Accordingly, the diagnosis and management of these disorders can be exceptionally difficult. A detailed discussion of gastrointestinal tract functions, disorders, causes, and treatments can be found in Spiro, *Clinical Gastroenterology* (3d. edition 1983).

Among the chronic disorders of the upper gastrointestinal tract are those which fall under the general categories of gastritis and peptic ulcer disease. (The upper gastrointestinal tract as used herein is defined as including the esophagus, the stomach, the duodenum and the jejunum.) Gastritis is, by definition, typified by an inflammation of the stomach mucosa. In practice, though, the disorder is manifested by a broad range of poorly-defined, and heretofore inadequately treated, symptoms such as indigestion, "heart burn", dyspepsia and excessive eructation. A general discussion of gastritis appears in B. J. Marshall and J. R. Warren, "Unidentified Curved Bacilli in the Stomach of Patients with Gastritis and Peptic Ulceration", *The Lancet*, (1984), pp. 1311-1315, and in R. Greenlaw, et al., "Gastroduodenitis, A Broader Concept of Peptic Ulcer Disease", *Digestive Diseases and Sciences*, Vol. 25 (1980), pp. 660-672.

Peptic ulcers are lesions of the gastrointestinal tract lining, characterized by loss of tissue due to the action of digestive acids and pepsin. It has been generally held that peptic ulcers are caused either by gastric hypersecretion, or (more often) by decreased resistance of the gastric lining to digestive acids and pepsin. The medical literature is replete with methods for treating ulcers, including modification of the diet, surgical removal of the lesions, and the use of drugs. Such drugs include; antacids, which serve to counteract excess gastric secretions; anticholinergics, which reduce acid secretion; $H_2$ antagonists, which also block the release of gastric acids; prostaglandins, which increase the resistance of the gastric lining to digestive fluids, and may also inhibit acid secretion; prokinetic agents, which enhance gastrointestinal tract motility; and compositions which form protective barriers over gastric lesions. Prescription and non-prescription drug therapies are generally described in Garnet, "Antacid Products", *Handbook of Non-prescription Drugs*, 7th edition (1982), Chapter 3.

Regardless of the particular drug composition used in treating gastrointestinal disorders, such as gastritis or peptic ulcer disease, the treatment is often imprecise and incomplete. Actual "cures", i.e., successful treatment resulting in total remission of disease, are very often not effected. See A. J. McLean, et al., "Cyto-protective Agents and Ulcer Relapse", 142 *The Medical Journal of Australia*, Special Supplement S25-S28 (1985). Furthermore, many conventional treatments may render subject hypochlorhydric (i.e., with low levels of hydrochloric acid in the stomach) which may predispose them to other disorders, e.g., gastrointestinal infection, halitosis, and gastric carcinomas.

Nitrofurantoin is a well-known antibacterial compound and has been used extensively as an active ingredient in antibacterial pharmaceutical compositions. See, for example, Mintzer, S., E. R. Kadison, W. H. Shlaes & O. Felsenfeld, "Treatment of Urinary Tract Infections with a New Antibacterial Nitrofuran", *Antibiotics & Chemotherapy*, Vol. 3, No. 2 (Feb., 1953), pp. 151-157; Richards, W. A., E. Riss, E. H. Kass & M. Finland, "Nitrofurantoin-Clinical and Laboratory Studies in Urinary Tract Infections", *Archives of Internal Medicine*, Vol. 96 (1955), pp. 437-450; Eudy, W. W., "Correlations Between In Vitro Sensitivity Testing and Therapeutic Response in Urinary Tract Infections", *Urology*, Vol. II, No. 5 (Nov., 1973), pp. 519-587; Bush, I. M., W. I. Metzger, I. Garlovsky, R. B. Bush, R. J. Ablin & N. Sadoughi, "Urinary Tract Infection-Antibacterial Susceptibility Patterns", *Urology*, Vol. III, No. 6 (Jun., 1974), pp. 697-700; Dickey, L., "A Comparison of the In Vitro Effectiveness of Nitrofurantoin and Five Antibiotics Against Bacteria from Urinary Tract Infections", *American Journal of Medical Technology*, (Sept.-Oct., 1961), pp. 273-279; Karmali, M. A., S. DeGrandis & P. C. Fleming, "Antimicrobial Susceptibility of *Campylobacter jejuni* with Special Reference to Resistance Patterns of Canadian Isolates", *Antimicrobial Agents and Chemotherapy*, Vol. 19, No. 4 (1981), pp. 593-597. allergic response) commensurate with a reasonable benefit/risk ratio when used in the manner of this invention. The specific "safe and effective amount" will, obviously, vary with such factors as the particular condition that is being treated, the physical condition of the patient, the nature of concurrent therapy (if any), and the specific formulations employed in the present invention. Specifically, the processes of the present invention, for the treatment and prophylaxis of a human or lower animal subject having an infectious gastrointestinal disorder, comprise the step of administering to said subject a safe and effective amount of nitrofurantoin.

As used herein, "infectious gastrointestinal disorder" encompasses any disease or other disorder of the upper gastrointestinal tract of a human or lower animal which is caused or mediated by *Campylobacter*-like (renamed *Helicobacter*) organisms (herein "CLO"), e.g., *Campylobacter pyloridis* (renamed *Helicobacter pylori*). Such CLO include those described in J. R. Warren and B. J. Marshall, "Unidentified Curved Bacilli on Gastric Epithelium in Active Chronic Gastritis", *The Lancet*, (1983), pp. 1273-1275, incorporated by reference herein, and G. Kasper and N. Dickgiesser, "Isolation from Gastric Epithelium of Campylobacter-like Bacteria that are Distinct from 'Campylobacter Pyloridis'", *The Lancet*, (1985), pp. 111-112. Such infectious gastrointestinal disorders include, for example: CLO-mediated disorders not manifested by presence of ulcerations in the gastric mucosa (herein "non-ulcerative gastrointestinal disorder"), including chronic or atrophic gastritis, non-ulcer dyspepsia, esophogeal reflux disease and gastric motility disorders; and "peptic ulcer disease", i.e., CLO-mediated gastric, duodenal, and jejunal ulcers.

As used herein, "administering" refers to any method which, in sound medical practice, delivers the compounds or compositions used

SUMMARY OF THE INVENTION

It is an object of the present invention to provide novel methods of treating infectious gastrointestinal disorders of the upper gastrointestinal tract of a human or lower animal which are caused or mediated by Campylobacter-like organisms.

It is also an object of the present invention to provide novel methods for preventing recurrence of infectious gastrointestinal disorders of the upper gastrointestinal tract of a human or lower animal which are caused or mediated by Campylobacter-like organisms.

The present invention involves methods for the treatment of a human or lower animal subject having an infectious gastrointestinal disorder or for prevention of recurrence of such disorder comprising the step of administering to such subject a safe and effective amount of nitrofurantoin.

DETAILED DESCRIPTION OF INVENTION

The methods of the present invention comprise treatment of humans or lower animals, having infectious gastrointestinal disorders, by administering nitrofurantoin. Specific compositions to be used in the processes of the present invention must, accordingly, be pharmaceutically acceptable. As used herein, a "pharmaceutically-acceptable" component is one which is suitable for use with humans and/or animals without undue adverse side effects (such as toxicity, irritation, and allergic response) commensurate with a reasonable benefit/risk ratio. Further, as used herein, the term "safe and effective amount" refers to the quantity of a component which is sufficient to yield a desired therapeutic response without undue adverse effects (such as toxicity, irritation, or in this invention to the subject to be treated in such a manner so as to be effective in the treatment or prophylaxis of the infectious gastrointestinal disorder. Preferably, the nitrofurantoin is administered orally.

As used herein, "prophylaxis" refers to the prevention of the occurrence of infectious gastrointestinal disorders in human or lower animals. While the methods of the present invention could be used for the prevention of such disorders in any human or lower animals, it is preferred to use the prophylactic treatment of nitrofurantoin in subjects which have a history of recurring infectious gastrointestinal disorders.

As used herein, "nitrofurantoin" is the compound which has the chemical structure:

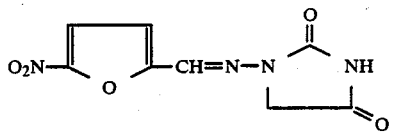

or its pharmaceutically acceptable salts, hydrates, or complexes. As used herein, nitrofurantoin "complexes" refer to chemical complexes of nitrofurantoin with other chemical constituents which result in entities which retain at least a substantial portion of the antimicrobial activity of nitrofurantoin. Examples of such complexes include nitrofurantoin-phthaloyl glycine and nitrofurantoin-phthaloyl aminocaproic acid.

Nitrofurantoin has been found to have a high degree of antimicrobial activity against Campylobacter-like bacteria, especially *Campylobacter pyloridis*. This activity of nitrofurantoin is surprising in light of the finding that related antibacterial substances have substantially less activity than nitrofurantoin against Campylobacter-like organisms including *Campylobacter pyloridis*. Also, other antibacterial substances known to be useful in combatting the same types of bacterial infections for which nitrofurantoin is commonly used and other antibacterial substances commonly used for treatment of gastrointestinal disorders have substantially less activity than nitrofurantoin against Campylobacter-like organisms including *Campylobacter pyloridis*.

The methods of the present invention involve the administration of a safe and effective amount of nitrofurantoin to a human or lower animal for the treatment or prophylaxis of infectious gastrointestinal disorders. The preferred daily dosage of nitrofurantoin is from about 1 mg to about 600 mg of nitrofurantoin per day, especially preferred is from about 10 mg to about 400 mg of nitrofurantoin per day, more preferred still is from about 20 mg to about 200 mg of nitrofurantoin per day.

The methods of the present invention for treatment of infectious gastrointestinal disorders preferably involve the administration of the above daily doses of nitrofurantoin until the disorder has been eradicated from the human or lower animal. It is preferred that the daily dosages be administered to the human or lower animal for a period of from about 1 day to about 200 days, more preferably from about 3 days to about 60 days, more preferably still from about 7 days to about 30 days.

The methods of the present invention for prophylaxis of infectious gastrointestinal disorders preferably involve the administration of the above doses of nitrofurantoin on a daily or less frequent basis in order to prevent recurrence of the disorder in the human or lower animal. It is preferred that the dosages be administered to the human or lower animal daily from about 1 day to about 200 days, more preferably from about 7 days to about 150 days, more preferably still from about 30 days to about 100 days. It is also preferred that the dosages be administered to the human or lower animal every 2 or 3 days for from about 7 days to about 400 days, more preferably from about 30 days to about 300 days, more preferably still from about 60 days to about 200 days. It is also preferred that the dosages be administered to the human or lower animal about weekly for a period of from about 14 days to about 800 days, more preferably from about 30 days to about 600 days, more preferably still from about 60 days to about 400 days.

Optional Components and Methods:

The methods of this invention may incorporate optional steps modifying the methods of treatment of this invention. Such optional steps may also utilize optional components or compositions. Such optional components or compositions must not, however, adversely affect the therapeutic activity of the nitrofurantoin used in the present methods.

A preferred method of this invention includes a diagnostic step for the detection of a CLO infection in the upper gastrointestinal tract of the human or lower animal subject by taking a biopsy of the affected tissue and identifying the presence of the CLO organism by conventional histological examination, e.g. fixing the tissue in paraffin for Hematoxylin and Eosin stain and in plastic for Warthin Starry Silver stain. (See Steer, H. W. and D. G. Colin-Jones, "Mucosal changes in gastric ulceration and their response to carbenoxolone sodium", *Gut*, Vol. 16 (1975), pp. 590–597; McNulty, C.

A. M. and D. M. Watson, "Spiral Bacteria of the Gastric Antrum", *The Lancet*, Vol. 1, No. 8385 (May, 1984), pp. 1068-1069; Jones, D. M., A. M. Lessells and J. Eldridge, "Campylobacter like organisms on the gastric mucosa: culture, histological, and serolopical studies", *Journal of Clinical Pathology*, "Vol. 37 (1984), pp. 1002-1006; Rollason, T. P., J. Stone and J. M. Rhodes, "Spiral organisms in endoscopic biopsies of the human stomach", *Journal of Clinical Pathology*, Vol. 37 (1984), pp. 23-26.) This diagnostic step is preferably performed prior to the step of administering nitrofurantoin. Also preferably, the diagnostic step is repeated during the step of administering the nitrofurantoin, and the step of administering the nitrofurantoin is terminated after the diagnostic step yields a negative result, unless prophylactic treatment of the human or lower animal is desired.

The following non-limiting examples illustrate the methods of the present invention.

EXAMPLE I

A human subject, suffering from atrophic gastritis, is treated by a method of the present invention. Specifically, the subject is endoscoped and a biopsy taken of the gastric mucosa of the subject. Analysis of the biopsy sample shows inflammation of the mucosa, and depletion of the protective mucous layer. Histological examination of the sample also reveals the presence of *Campylobacter pyloridis*. The subject is then treated, according to the present invention, by administering a composition containing nitrofurantoin, sold by Norwich Eaton Pharmaceuticals, Inc. under the name "Furadantin". The composition, in oral suspension form, is administered 4 times daily in equal doses of 100 milligrams (for a total of approximately 400 milligrams of nitrofurantoin administered per day) for 14 days. Thereafter, the subject is endoscoped and biopsied again, finding essentially normal, healed gastric mucosa. Histological examination of the gastric material sample does not reveal any bacterial infection. The subject remains asymptomatic, and another biopsy performed five months later reveals normal gastric mucosa.

EXAMPLE II

A human subject, suffering from peptic ulcer disease, is treated by a method of the present invention. Specifically, a biopsy of gastric mucosa is taken from the stomach of the subject. Histological examination of the mucosa reveals the presence of a Campylobacter-like organism.

The subject is then treated by orally administering 100 milligrams of nitrofurantoin in capsule form per day for 30 days. Thereafter, the subject is endoscoped, revealing normal gastric mucosa and healing of the peptic ulcer crater.

EXAMPLE III

A human subject, with a history of periodic recurring peptic ulcer disease but not currently suffering from such disease, is treated by a method of the present invention. A biopsy of gastric mucosa taken from the stomach of the subject reveals no presence of any Campylobacter-like organisms. The subject is then treated by orally administering 25 mg of nitrofurantoin in tablet form every 3 days for 365 days. The subject remains free of symptoms of peptic ulcer disease over the entire period; biopsies taken periodically which are histologically examined show no presence of Campylobacter-like organisms.

While particular embodiments of the present invention have been described, it will be obvious to those skilled in the art that various changes and modifications of the methods of the present invention for treating infectious gastrointestinal disorders can be made without departing from the spirit and scope of the invention. It is intended to cover, in the appended claims, all such modifications that are within the scope of this invention.

What is claimed is:

1. A method for the treatment of a human subject having an infectious gastrointestinal disorder of the stomach or duodenum which is caused or mediated by *Campylobacter pyloridis* (renamed *Helicobacter pylori*) comprising the step of administering to said subject a safe and effective amount of nitrofurantoin.

2. The method of claim 1 wherein said infectious gastrointestinal disorder is of the stomach, and said nitrofurantoin is administered orally.

3. The method of claim 1 wherein said infectious gastrointestinal disorder is of the duodenum, and said nitrofurantoin is administered orally.

4. The method of claim 1 wherein said nitrofurantoin is administered at a level of from about 10 mg to about 400 mg per day for from about 3 days to about 60 days.

5. The method of claim 1 wherein said nitrofurantoin is orally administered at a level of from about 20 mg to about 400 mg per day for from about 7 days to about 60 days.

6. The method of claim 1 wherein said infectious gastrointestinal disorder is a non-ulcerative gastrointestinal disorder.

7. The method of claim 5 wherein said infectious gastrointestinal disorder is a non-ulcerative gastrointestinal disorder.

8. The method of claim 2 wherein said infectious gastrointestinal disorder is gastritis.

9. The method of claim 5 wherein said infectious gastrointestinal disorder is gastritis.

10. The method of claim 1 wherein said infectious gastrointestinal disorder is peptic ulcer disease.

11. The method of claim 5 wherein said infectious gastrointestinal disorder is peptic ulcer disease.

* * * * *

UNITED STATES PATENT AND TRADEMARK OFFICE
CERTIFICATE OF CORRECTION

PATENT NO. : 4,959,384
DATED : September 25, 1990
INVENTOR(S) : WILLIAM G. KRAFT and DONNA R. MORGAN It is certified that error appears in the above-identified patent and that said Letters Patent is hereby corrected as shown below:

Delete the entire text in column 2, lines 30 through 68, starting with "allergic response)" and ending with "compositions used" and insert the same entire text in Column 3, line 35, between "irritation, or" and "in this invention".

Signed and Sealed this

Tenth Day of November, 1992

Attest:

DOUGLAS B. COMER

*Attesting Officer*  *Acting Commissioner of Patents and Trademarks*